United States Patent [19]

Lee

[11] Patent Number: 5,698,744
[45] Date of Patent: Dec. 16, 1997

[54] PROCESS FOR THE SELECTIVE OXIDATION OF COMPOUNDS

[75] Inventor: Ross Albert Lee, Chesapeake City, Md.

[73] Assignee: E. I. Du Pont de Nemours and Company, Wilmington, Del.

[21] Appl. No.: 414,966

[22] Filed: Mar. 31, 1995

[51] Int. Cl.$^6$ ............................................. C07C 45/29
[52] U.S. Cl. .................. 568/322; 568/403; 568/485; 568/442
[58] Field of Search ...................... 568/322, 403, 568/485, 442

[56] References Cited

U.S. PATENT DOCUMENTS 3,512,930  5/1970  Bottjer et al. .................. 23/145
3,954,666  5/1976  Marquisee et al. ............... 252/430
4,524,008  6/1985  Chen .......................... 252/62.56

OTHER PUBLICATIONS

Fatiadi, Synthesis, 1976, "Active Manganese Dioxide Oxidation In Organic Chemistry" Part I and Part II, pp. 65–104, 133–167.

Primary Examiner—James H. Reamer

[57] ABSTRACT

Selective oxidation employs ferromagnetic chromium dioxide followed by magnetic separation.

6 Claims, No Drawings

PROCESS FOR THE SELECTIVE OXIDATION OF COMPOUNDS

FIELD OF THE INVENTION

This invention relates to a process for the selective oxidation of compounds. More particularly, it relates to a process for the selective oxidation of organic compounds in which ferromagnetic chromium dioxide is used as the oxidant and recovered by magnetic separation.

BACKGROUND OF THE INVENTION

Oxidations are key processes in the manufacture of many commercially important materials, including agrichemicals, pharmaceuticals, plastics, etc. Commonly used oxidants include aqueous chromic acid, aqueous potassium permanganate and activated manganese dioxide. With each of these oxidants, however, there are some disadvantages. Separation of the oxidized product from the oxidant and its reduced form is often labor intensive and inefficient, resulting in poor yields. In some cases, the oxidant is not very selective. The oxidation reaction may not stop at the desired product. For example, in the oxidation of a primary alcohol to an aldehyde, the oxidation reaction may proceed to the formation of the acid. In addition, the oxidant may oxidize additional functionality in a multi-functional compound. This lack of selectivity complicates separation processes and leads to lower yields. Furthermore, the selectivity of the oxidant may depend critically on the method of preparation.

Fatiadi in *Synthesis*, 1976, pp. 65–167, discloses the utility of activated manganese dioxide in selective oxidations. However, the effectiveness of manganese dioxide oxidations is dependent on the method of preparation of the manganese dioxide. In addition, severe separation difficulties can arise in these reactions. Marquise et al., U.S. Pat. No. 3,954,666, disclose the utility of the magnetic separation of reactants. In this patent, a heterogeneous catalyst and a ferromagnetic material were encapsulated in a semipermeable polymeric microcapsule. After reaction with an oxidizable material, the microcapsules were removed by separating them magnetically. However, the oxidants described have poor selectivity, and the encapsulation process is costly and time-consuming. Bottjer et al., U.S. Pat. No. 3,512,930, disclose a test for the effectiveness of a protective barrier on chromium dioxide particles, in which the unprotected chromium dioxide oxidizes benzhydrol to benzophenone. However, only initial reaction rates were obtained for the test, and there is no discussion of the overall selectivity of the reaction. There exists a need, therefore, for an improved process for the selective oxidation of compounds which overcomes the disadvantages of the oxidants enumerated above.

SUMMARY OF THE INVENTION

This invention provides a process for the selective oxidation of an oxidizable compound, comprising the steps:

(a) mixing ferromagnetic chromium dioxide with the oxidizable compound;

(b) allowing the mixture in (a) to react to produce reduced chromium compounds adhering to unreacted chromium dioxide and oxidized products; and (c) magnetically separating the chromium dioxide with the reduced chromium compounds from the oxidized products.

In another embodiment, the process further comprises:

(d) regenerating the chromium dioxide by heating in air the chromium dioxide with the reduced chromium compounds separated in step (c).

DETAILED DESCRIPTION OF THE INVENTION

This invention relates to a process for the selective oxidation of certain compounds. The oxidant in the process is chromium dioxide. Surprisingly and unexpectedly, it has been found that chromium dioxide is a mild and selective oxidant. In the oxidation reaction, the chromium dioxide is a reactant and not a catalyst, and thus reduced chromium species are formed. It also has been found that essentially all the chromium, i.e., the unreacted ferromagnetic chromium dioxide and the non-ferromagnetic reduced chromium species, can be separated from the reaction mixture magnetically. Thus, the chromium dioxide oxidant provides both selectivity of oxidation and ease of separation of reaction products.

In practicing the invention, any preformed ferromagnetic chromium dioxide can be used. Suitable ferromagnetic chromium dioxide and its preparation has been described in numerous patents, including U.S. Pat. Nos. 2,885,365, 2,923,684, 2,923,684, 2,956,955, 3,034,988, 3,117,093, 3,278,263, 3,911,095, 4,524,008, 4,698,220 and 4,769,165, among others. A preferred process is given in U.S. Pat. No. 4,524,008, which is hereby incorporated by reference. The chromium dioxide should be in the form of finely divided particles to provide sufficient surface area for reaction. The lower limit on the particle size desirable in the process of the invention is that size which can be effectively removed from the reaction medium by the application of a magnetic field. The presence of larger-sized particles does not deleteriously affect the process other than in reducing the reaction rate. In general, it is preferred that the chromium dioxide have a specific surface area (SSA) no greater than 60 $m^2/g$; more preferably an SSA of 15–40 $m^2/g$.

It is preferred that the chromium dioxide have an untreated surface. In many cases, chromium dioxide which is to be used in magnetic tape applications, is given a surface passivation or stabilization treatment. This is described in, e.g., Bottjer et al., U.S. Pat. No. 3,512,930. The objective of such a treatment is to reduce the oxidative reactivity of the surface of the particles, while maintaining the magnetic properties. In the process of the present invention, it is the oxidative reactivity as well as the magnetic properties of the chromium dioxide which are important. Therefore, any treatment which reduces the oxidative reactivity of the chromium dioxide particles is counterproductive.

The oxidation reaction produces a reduced form of the chromium. This usually is an oxy-hydroxide of Cr(III). It has been found that this reduced chromium remains with the crystalline particles of chromium dioxide and is magnetically separable with them. That is, even though the Cr(III) compound is not ferromagnetic, it is removed with the chromium dioxide when a magnet is applied.

The chromium dioxide reacts with an oxidizable compound. Suitable oxidizable organic compounds include alcohols. With most oxidants, primary alcohols are oxidized all the way to carboxylic acids, and it is difficult to isolate much of the intermediate aldehyde. Chromium dioxide selectively oxidizes primary alcohols to aldehydes. This is true of many simple alcohols, such as primary alkyl alcohols. However, it is particularly advantageous to use activated alcohols. As used herein, "activated alcohol" is intended to mean an alcohol which has an electron-rich source in the position adjacent to the hydroxy group. Examples of electron-rich sources include alkenic, alkynic, aromatic, alicyclic and carbonyl groups. Secondary alcohols are also suitable oxidizable organic compounds, and are oxidized to ketones.

Examples of activated alcohols include benzylic alcohols, heterobenzylic alcohols, allylic alcohols, propargylic alcohols, α-hydroxy ethers, phenols, and enolizable ketones.

Suitable oxidizable organic compounds include oxidizable hydrocarbons where direct oxidation of methyl, methylene or methine groups (i.e., compounds having a tertiary hydrogen, $R_3C-H$) produces either hydroxyl, carbonyl, ether, coupled or dehydrogenated products. Preferably, the group to be oxidized is activated as described above for alcohols. Examples of suitable oxidizable organic compounds include polynuclear aromatics, such as anthracene and fluorene, heteronucleararomatics, hydrogenated aromatics and hydrogenated heteroaromatics.

Suitable oxidizable organic compounds include oxidizable leuco dyes. The leuco form of a dye is the reduced form of the dye having one or two hydrogen atoms, the removal of which, together with an additional electron in certain cases, produces the dye, or colored form. Such leuco dyes have been described, for example, in U.S. Pat. Nos. 3,445,234, 4,247,618, and 4,622,286. Examples of leuco dyes include triarylmethanes, modified diarylmethanes and heteroarylmethanes.

Other types of compounds which can function as suitable oxidizable organic compounds in the process of the invention include organic amines, organosulfur, organophosphorus and heterocyclic compounds. Suitable non-organic oxidizable compounds include metal sulfites, hydrogen sulfide and inorganic phosphorus compounds.

In the process of the invention, the oxidizable compound is brought into contact with the chromium dioxide oxidant and allowed to react. This can be carried out by any conventional means for mixing two reactants. Generally, it is accomplished by mixing the two components together in a suitable solvent. The reaction can take place at room temperature, or with heating. In some cases it may even be necessary to cool the reaction if it is particularly exothermic. The time of reaction will depend on the nature of the organic compound to be oxidized, the solvent, temperature and the particle size and amount of chromium dioxide. In general, the reactions can be carried out by refluxing in a solvent such as methylene chloride for a few hours.

After the oxidation reaction is complete, the chromium products are separated from the organic reaction products magnetically. The principles of magnetic separation of materials are well known and discussions can be found in many standard engineering references, e.g., the *Chemical Engineers' Handbook* (Fifth edition, McGraw-Hill, 1973). In general, the separation can be accomplished simply by exposing the reaction vessel to a magnet. The unreacted chromium dioxide and the associated chromium reduction products will move to the location of the magnet. The magnet can be placed internally, i.e., within the reaction vessel. A magnetic stirrer is frequently sufficient to effect separation. To facilitate recovery of the chromium-containing products, it is preferable to have the magnet placed externally, i.e., on the outside of the reaction vessel. Any type of magnet can be used as long as it has sufficient strength to attract essentially all the chromium products. This is most readily ascertained visually. When the magnet is present, if it has sufficient strength, the dark chromium products will essentially all be removed from the reaction mixture and the mixture will be clarified.

After the chromium products have been attracted by the magnet and while they are held in place, it is possible to simply pour off the non-magnetic portion of the mixture, e.g., decant off the liquid phase(s). The desired oxidation product can then be separated and purified by any conventional method, e.g., distillation, chromatography, crystallization, etc.

The chromium products can then be recovered, most easily if the magnet was external to the reaction vessel. It is possible to regenerate the chromium dioxide, and thus the oxidative reactivity, by first removing any solvent that may be present and then heating the chromium-containing material in the presence of an oxidizing agent, as described in U.S. Pat. No. 3,529,930. The regeneration is preferably accomplished by heating in air at temperatures in the range of 200°–400° C. for a few hours.

The process of the invention is illustrated, but not limited by the following examples.

EXAMPLES

Examples 1–8

These examples illustrate the process of the invention in oxidizing activated alcohols (Examples 1, 2, 4, 5, 7 and 8), non-activated alcohols (Example 2), and activated hydrocarbons (Example 6). The selectivity of the chromium dioxide in stopping at the aldehyde is shown in Examples 2, 3, 4 and 5. The selectivity of the chromium dioxide in oxidizing the alcohol without attacking other functionalities in the compound is shown in Examples 4 and 5.

A 200-ml round-bottomed flask equipped with a water-cooled condenser and Vibro Mixer\(Chemapec, Inc., Hoboken, N.J.) was charged with a slurry of 10 g chromium dioxide (prepared as described in U.S. Pat. No. 4,524,008, Example 2, without a surface stabilization treatment) and 35 ml of solvent. A solution of 1.0 g of the compound to be oxidized in 15 ml of solvent was added to the mixture and heated at reflux for 2.5–3 hours.

The reaction mixture was then cooled to room temperature. To separate the oxidation products from the chromium products, a strong magnet (a horseshoe magnet 2 in. across and ⅜ in. thick, 2000–5000 gauss) was placed on one side of the flask and the liquid was decanted off. The remaining chromium solids were rinsed with additional solvent and the rinse liquids added to the decantate. The solvent was then stripped off on a rotary evaporator. The resulting products isolated were analyzed and identified by one or more of the following techniques: IR or UV spectroscopy, gas chromatography (GC). The results are given in the table below.

| Ex. | Oxidizable Compound | Solvent | Product | Yield (Analysis) |
| --- | --- | --- | --- | --- |
| 1 | benzhydrol | $MeCl_2$ | benzophenone | 40% (UV) |
| 2 | benzyl alcohol | $MeCl_2$ | benzaldehyde | ¾ 80% (IR, GC) |
| 3 | 1-octyl alcohol | $MeCl_2$ | 1-octanal | ● 40% (IR, GC) |
| 4 | geraniol | $MeCl_2$ | citral | ¾ 95% (IR) |
| 5 | cinnamyl alcohol | $MeCl_2$ | cinnamaldehyde | ¾ 75% (IR) |
| 6 | anthracene | THF | anthraquinone | ¾ 25% (IR) |
| 7 | benzoin | $MeCl_2$ | benzil | ● 33% (IR) |
| 8 | benzoin | acetone | benzil | |

$MeCl_2$ = mmethylene chloride
THF = tetrahydrofuran

Example 9

This example illustrates the oxidation of a leuco dye to the dye form. It also is an illustration of the oxidation of an activated hydrocarbon.

A 500-ml round-bottomed flask equipped with a water-cooled condenser was charged with a slurry of 100 g chromium dioxide (prepared as described in Examples 1-8) and 350 ml of methylene chloride. A solution of 10 g of a leuco green dye, bis(4-diethylamino-2-methylphenyl) phenylmethane, in 150 ml of methylene chloride and 4.54 g p-toluensulfonic acid was added to the mixture. The mixture was placed in an ultrasonic bath for 3 hours. Enough heat was generated by the reaction to reflux the methylene chloride. The reaction products were separated from the chromium-containing materials as described in Examples 1-8.

The oxidation product was the green dye form as analyzed by TLC and visible spectrum (max at 658 nm). The yield was greater than 75%.

Examples 10-11

These examples demonstrate that the chromium dioxide of this invention is equivalent in oxidizing ability to the common oxidant activated manganese dioxide, which is not magnetically retrievable.

A slurry consisting of 10.0 g oxidant, 1.0 g benzyl alcohol and 25 ml of methylene chloride was stirred and heated at reflux for four hours in a 100 ml, 3-necked flask equipped with a reflux condenser and a mechanically rotated 25 mm Teflon\paddle.

In Example 10 the oxidant was chromium dioxide prepared as described above. Product separation was carried out as described in Examples 1-8. The oxidation product was identified as benzaldehyde in 75% yield, free of benzyl alcohol as indicated by the NMR spectrum of the total crude product.

In Example 11 the oxidant was activated manganese dioxide (Aldrich Chemical Co., catalog no. 21,764-6, Milwaukee, Wis.). Because the oxidant was not magnetic, it was removed by filtration of the reaction slurry through a porous glass filter. The filter cake was washed with about 15 ml of methylene chloride and the washes were combined with the original filtrate. The oxidation product was isolated by removal of the methylene chloride by evaporation under vacuum. Benzaldehyde, free of benzyl alcohol by NMR spectroscopy, was obtained in 57% yield.

Example 12

This example illustrates the regeneration of the chromium dioxide from the chromium reaction products.

The solids retained by the magnet in Example 2 were dried, and heated in air for two hours at 385° C. Example 2 was then repeated using this chromium material. After only one hour of refluxing in methylene chloride, an IR spectrum indicated that the liquid phase contained predominantly the oxidized product, benzaldehyde.

What is claimed is:

1. A process for the selective oxidation of an oxidizable compound by ferromagnetic chromium dioxide, comprising the steps:

(a) mixing the ferromagnetic chromium dioxide with the oxidizable compound;

(b) allowing the mixture in (a) to react to produce reduced chromium compounds adhering to unreacted chromium dioxide and oxidized products; and (c) magnetically separating the chromium dioxide with the reduced chromium compounds from the oxidized products, wherein the oxidizable compound is selected from the group consisting of alcohol; oxidizable hydrocarbon having at least one methyl, methylene or methine group; oxidizable leuco dye; organic amine; organosulfur compound; organophosphorus compound; heterocyclic compound; metal sulfite; hydrogen sulfide; and inorganic phosphorus compound.

2. The process of claim 1 wherein the oxidizable organic compound is an activated alcohol selected from the group consisting of benzylic alcohols, heterobenzylic alcohols, allylic alcohols, propargylic alcohols, α-hydroxy ethers, phenols, and enolizable ketones.

3. The process of claim 1 wherein the oxidizable organic compound is an activated hydrocarbon selected from the group consisting of polynuclear aromatics, heteronucleararomatics, hydrogenated aromatics and hydrogenated heteroaromatics.

4. The process of claim 1 wherein the oxidizable organic compound is a leuco dye selected from the group consisting of triarylmethanes, modified diarylmethanes and heteroarylmethanes.

5. The process of claim 1 which further comprises the step (d) regenerating the chromium dioxide by heating in air the chromium dioxide with the reduced chromium compounds separated in step (c).

6. The process of claim 5 wherein step (d) is carried out at a temperature of 200°–400° C.

* * * * *